United States Patent [19]

Blum

[11] 4,266,543
[45] May 12, 1981

[54] HYPODERMIC NEEDLE PROTECTION MEANS

[76] Inventor: Alvin S. Blum, 2350 Del Mar Pl., Fort Lauderdale, Fla. 33301

[21] Appl. No.: 13,911

[22] Filed: Feb. 22, 1979

[51] Int. Cl.³ .............................................. A61M 5/00
[52] U.S. Cl. ............................... 128/218 N; 128/221; 128/763
[58] Field of Search ................... 128/215, 216, 218 N, 128/221, 763, 764

[56] References Cited

U.S. PATENT DOCUMENTS

| | | | |
|---|---|---|---|
| 561,059 | 5/1896 | Mitchell et al. | 128/218 N |
| 2,693,186 | 11/1954 | Riker et al. | 128/218 F |
| 2,845,065 | 7/1958 | Gabriel | 128/215 |
| 3,094,989 | 6/1963 | Stauffer | 128/218 F |
| 3,612,051 | 10/1971 | Arce | 128/215 |
| 3,886,930 | 6/1975 | Ryan | 128/764 |
| 4,139,009 | 2/1979 | Alvarez | 128/218 N |

FOREIGN PATENT DOCUMENTS 585862 10/1959 Canada ................................ 128/218 F

*Primary Examiner*—John D. Yasko

[57] ABSTRACT

Hypodermic needle protection means comprising in an embodiment for vacuum tube sampling: a first needle slidably contained within a second needle, and firmly fastened therein by fastening means. Said fastening means can be overcome by forcing the point of the first needle against a hard surface to move said outer needle over said inner needle thereby covering its point. In an embodiment for a hypodermic needle comprising: a needle slidably contained within a housing and firmly fastened therein by fastening means. Said fastening means can be overcome by forcing the point of said needle against a hard surface to move said housing over said needle, thereby covering its point.

10 Claims, 4 Drawing Figures

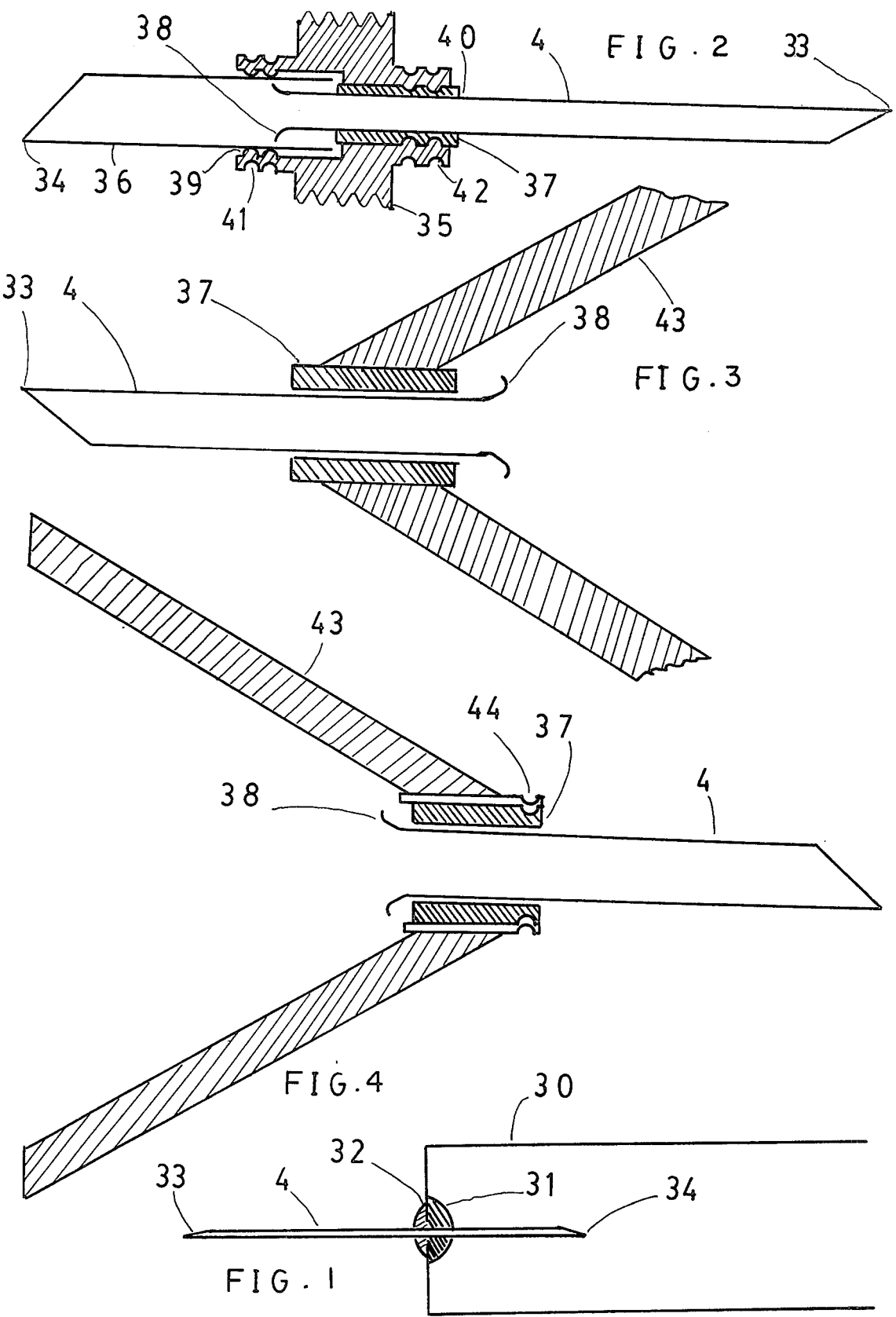

HYPODERMIC NEEDLE PROTECTION MEANS

BACKGROUND OF THE INVENTION

1. Field of the Invention

The invention relates to hypodermic needles, syringes, infusion and blood drawing apparatus and means for protecting people from accidental contaminated needle puncture.

2. Description of the Prior Art

Disposable hypodermic syringes are packaged with attached needles and sometimes needles are packaged separately. In either case, the needle is packaged with a separate sheath or protective covering. In normal use the syringe is removed from its sterile package and the needle sheath is left on the sterile needle that is attached to the syringe either at the factory or by the user. The sheath is temporarily removed while the syringe is filled with liquid. The sheath is then replaced to protect the needle until ready for injection. The sheath is often misplaced in the hectic circumstances surrounding hypodermic use. Intravenous infusion sets also present problems with respect to needle protection. Since many hours, even a shift change, may elapse between exposing the needle for injection and final disposal of the needle, it is not surprising that the sheath cannot be found at bedside for safe needle disposal. When the needle is permanently attached to the tubing, it must be cut off to be placed in special needle disposal means. Consequently, the entire infusion set along with a bloody, exposed needle is often discarded in the nearest waste where it presents a hazard to the trash handlers. Vacuum tube apparatus for blood sampling uses a double ended needle for simultaneous puncture of tube and vein. It too employs a removable sheath and presents similar problems of disposal of the sharp, contaminated needle. Used needles are a common source of infectious disease, especially hepatitis, in hospital personnel. Hepatitis is a debilitating, life threatening illness. In many hospitals needle puncture is the most common industrial accident. It occurs most often when sheathing the needle and handling trash. A needle must be so constructed that there is no chance of it detaching from its hub and being lost within the patient. Needles are so well attached to their hubs that they will break when pressed at their points without yielding at the hub attachment.

SUMMARY OF THE PRESENT INVENTION.

In broad terms the invention is directed to improved means of covering a hypodermic needle. It is an object of the present invention to provide captive needle covering means. It is an object to provide needle covering means that can be applied from behind the point to protect the operator during the covering operation. It is an object to provide covering means that cannot fall off during disposal. It is an object to provide captive needle covering means that remain on the syringe and do not interfere with viewing syringe contents. Other objects and advantages of the present invention will readily come to mind as the following description to be read in cojunction with the several figures is developed.

BRIEF DESCRIPTION OF THE DRAWINGS

FIG. 1 is a diagrammatic cross section of an embodiment of the invention for use with evacuated blood collecting tubes.

FIG. 2 is a diagrammatic cross section of another embodiment of the invention for use with evacuated blood collecting tubes.

FIG. 3 is a diagrammatic cross section of a portion of a hypodermic needle assembly.

FIG. 4 is a diagrammatic cross section of another hypodermic needle assembly.

DESCRIPTION OF THE PREFERRED EMBODIMENTS

It is important that a hypodermic needle be so constructed that there is no chance of it accidentally detaching from its hub and being lost in the patient's body. Needles are provided so well attached to their hubs that they will break or bend when pressed at the point without yielding of the hub attachment. The following embodiments take advantage of the fact that a sharp needle will penetrate tissue and vial stoppers to perform its functions without the application of very great force. These embodiments provide needle attachments that hold at the forces required for normal use, but yield at greater force, allowing the attachments to slide down over the needle to cover its point. In effect, the hub and its attachments become the sliding needle covering means.

FIG. 1 shows a double ended needle 4 and holder 30 for use with an evacuated blood collecting tube of the Vacutainer type. A flange 31 is permanently fastened to needle 4 and meets inner surface of holder 30. Fastening means 32 holds needle 4 to holder 30 securely enough to withstand all forces involved in normal use. When a much greater force is applied by pressing needle point 33 against a hard surface, fastening means 32 yields by allowing needle 4 to slide into holder 30 until the point is flush with the surface of the holder. With the needle entirely within the holder, the combination is discarded. One means of accomplishing this is to cover the metal needle with a tight sleeve or silicone coat and then apply an adhesive plastic compound to form fastening means 32. Flange 31 resists forces applied to point 33 when puncturing rubber stopper of evacuated tube and preventing loss of needle in body. Fastening means 32 must remain fixed at the force required to puncture tissue. The yielding of fastening means 32 must be of the snug, sliding type, that is the needle must never be so loose that it will extend again by gravitational force. A resilient sleeve or coating between metal needle 4 and plastic seal 32 is a means of achieving this object.

FIG. 2 shows another embodiment of the invention for a double ended needle for blood drawing with evacuated tubes. Threaded metal member 35 screws into a female thread in a reusable plastic needle holder similar to holder 30 of FIG. 1. Smaller diameter needle 4 with patient point 33 on one end and flared or partially flattened at other end 38 and bearing resilient sleeve 37 slides into larger diameter needle 36 having stopper point 34. Member 35 has an axial hole with two diameters. On the patient side, diameter 40 is just large enough to admit needle 4 with sleeve 37, but too small to pass flattened or flared end 38. This prevents needle from ever being lost in patient. Larger diameter 39 at stopper end of hole allows introduction of needle 36. Swaging or crimping means at indentation 41 have connected needle 36 permanently to member 35, and crimping means at indentation 42 yieldably fastens needle 4 to member 35. Needle 4 must be fastened to member 35 so that it does not yield at the forces required to puncture tissue.

After use, the point 33 is pressed against a hard surface, and needle 4 slides in sleeve 37 and needle 36 until member 35 is flush with point 33. Dull, unsharp end 38 of needle 4 now projects beyond point 34 of needle 36 so that both ends are protected. The needle sheath that was part of the sterile package is now used to unscrew member 35 from its reusable plastic holder for discarding in the usual fashion, except that the operator is safe from puncture during the procedure.

In another embodiment of the invention, FIG. 3 shows a hypodermic needle 4 with point 33 in a molded plastic hub 43 having a standard Luer taper fitting for a syringe, infusion set, or the like. Needle 4 with snug resilient sleeve 37 is cemented or molded into hub 43 so that the resulting hole is too small to allow passage of flared or partially flattened end 38 of needle 4 thereby preventing loss of needle in body. Sleeve 37 grips needle 4 firmly enough that needle remains fixed at the forces normally required to puncture the rubber top of a pharmaceutical vial, but yields at a greater force, causing hub and its attachments to slide down to protect point 33. A standard 20 guage × 1 inch needle punctured vials at forces of 500 to 650 grams, while a force of 2650 grams did not deform the needle. If the connecting means were fabricated to yield at 1300 grams in this case, it would satisfy most puncturing requirements without yielding. After use, the syringe would be held by the barrel, and the point pressed against a hard surface until, at 1300 grams force, the hub and/or syringe would slide down needle 4 until flush with point 33, rendering the combination safer for disposal. Discarding the plunger separately prevents reuse.

In another embodiment of the invention for a needle and hub combination shown in FIG. 4, malleable metal sleeve 44 is molded into plastic hub 43. Hole in sleeve 44 allows passage of needle 4 with resilient sleeve 37 but blocks flared or partially flattened end 38. Metal sleeve 44 is crimped down against sleeve 37 resulting in yieldable fastening of needle 4. The hub and crimping sleeve may be fabricated in one piece. Careful control of the crimping operation and surface treatment of needle 4 may eliminate the need for sleeve 37.

While I have shown and described the preferred embodiments of my invention, it will be understood that the invention may be embodied other wise than as herein specifically illustrated or described, and that certain changes in the form and arrangement of parts and in the specific manner of practicing the invention may be made without departing from the underlying ideas or principles of this invention within the scope of the appended claims.

What is claimed is:

1. A hypodermic needle for syringes, infusion devices, and the like comprising: a hypodermic needle shaft having a distal pointed end for puncturing skin, medicament vial enclosures, and the like; needle support means at a proximal region of said shaft arranged to support the needle at the end of said syringe for use, said shaft being held within said support means by said fastening means arranged firstly to hold said needle under forces against said point necessary for ordinary usage and arranged secondly to yield slidably under some greater force against said point, causing said shaft to slide within said support means until said point is surrounded, protected and held in place by said support means.

2. The invention of claim 1 for blood sampling with an evacuated tube further comprising: a second point on said needle shaft for puncturing the closure of said evacuated tube, said point being at the proximal end of said shaft; said needle support means forming a sleeve around said proximal point to hold the top of said tube therein and provide a needle holder during venipuncture, said sleeve being long enough to protect the proximal point after the distal point has been forced to its protected position within said needle support means.

3. The invention of claim 1 for blood sampling with an evacuated tube comprising: a second pointed needle permanently fastened to said needle support means and facing in the opposite direction from the first point; the two needles being so arranged that the first needle will slide within said second needle upon yielding; and first needle being sufficiently longer than said second needle that the blunt end of said first needle extends beyond and protects thereby, the point of said second needle, thereby causing both points to be protected when the first point is forced into needle support means.

4. The invention of claim 1 wherein needle support means comprises a needle hub with conical connecting means for sealably fitting on a syringe, infusion set or the like.

5. The invention of claim 1 wherein needle support means is the end of a syringe, infusion device or the like.

6. The invention of claim 1 wherein yieldable fastening means includes resilient sleeve means on needle shaft.

7. The invention of claim 1 wherein yieldable fastening means includes controlled crimping means.

8. The invention of claim 1 wherein proximal end of needle shaft is enlarged by enlarging means to prevent its forward movement and loss through fastening means.

9. A hypodermic needle for blood sampling with evacuated tube means comprising: a hypodermic needle shaft having a distal pointed end for puncturing skin and the like; needle support means at a proximal region of said shaft arranged to support said needle shaft for use, said shaft being held to said needle support means by fastening means, said fastening means being arranged to firstly hold said needle under forces against said point necessary for ordinary usage and arranged secondly to yield slidably under some greater force against said point; a second pointed needle permanently fastened to said needle support means having a point facing in the opposite direction from said first point; said needles being so arranged that said first needle will slide within said second needle upon yielding.

10. The invention of claim 9 wherein said first needle is sufficiently longer than said second needle that the blunt end of said first needle extends beyond and protects thereby the point of said second needle upon yielding, thereby causing both points to be protected when the first point is forced into said needle support means.

* * * * *